United States Patent
Werner et al.

(10) Patent No.: US 6,313,323 B1
(45) Date of Patent: Nov. 6, 2001

(54) TRIMERIZATION OF FORMALDEHYDE IN THE GAS PHASE

(75) Inventors: Harald Werner, Bad Homburg; Elke Schweers, Bad Soden; Frank Olschewski, Unterliederbach; Gerhard Geiss, Liederbach; Elfriede Hufsky, Rodheim; Helmut Tränkler; Heinz Alexander, both of Frankfurt, all of (DE)

(73) Assignee: Ticona GmbH (DE)

( * ) Notice: Subject to any disclaimer, the term of this patent is extended or adjusted under 35 U.S.C. 154(b) by 0 days.

(21) Appl. No.: 09/564,877

(22) Filed: May 4, 2000

(51) Int. Cl.[7] .................................................. C07D 323/06
(52) U.S. Cl. ............................................................ 549/368
(58) Field of Search ............................................... 549/368

(56) References Cited

U.S. PATENT DOCUMENTS 5,508,448    4/1996    Emig et al. ........................... 549/368

FOREIGN PATENT DOCUMENTS 0 604 884    7/1994    (EP).
0 691 338    1/1996    (EP).

Primary Examiner—T. A. Solola
(74) Attorney, Agent, or Firm—Connolly Bove Lodge & Hutz LLP

(57) ABSTRACT

A process for the gas-phase trimerization of formaldehyde to give trioxane using solid phosphoric acid catalysts. Particularly suitable catalysts for this process are SPA catalysts (solid phosphorous acid), for example "silicon phosphates". The main advantage of this catalyst system is its simple and inexpensive production and ready availability and also, in particular, its improved long-term stability compared to the few previously described catalysts which are mostly based on supported heteropolyacids.

12 Claims, No Drawings

TRIMERIZATION OF FORMALDEHYDE IN THE GAS PHASE

The present invention relates to a process for producing trioxane from formaldehyde having a low water content in the gas phase, wherein a solid phosphoric acid catalyst is used in the trimerization of formaldehyde to give trioxane.

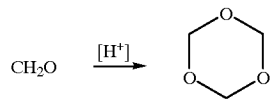

Trioxane is the most widely used starting material for the preparation of polyoxymethylene (POM). POM belongs to the group of polyacetals and is an industrially very valuable polymer with excellent properties. It displays high strength, stiffness, toughness (even at low temperatures) and dimensional stability and also good heat resistance, low water absorption capability, good electrical properties, good sliding and wear behavior and good processability.

In the industrial processes currently used for preparing formaldehyde (silver catalyst process or Formox process), formaldehyde is obtained as an aqueous solution. Trioxane is therefore usually prepared in the liquid phase from aqueous formaldehyde solutions (formalin) using mineral acids (e.g. sulfuric acid), or acid ion-exchange resins (e.g. sulfonated polystyrene).

A process based on formaldehyde having a low water content, i.e. completely or substantially anhydrous formaldehyde, is of great economic interest since considerable costs incurred in the preparation of trioxane according to the prior art as a result of numerous energy-intensive distillation steps and/or extraction steps can be avoided. Due to the lack of industrial availability of formaldehyde having a low water content, such a process for preparing trioxane in the gas phase has not yet been implemented in industry.

The industrial availability of formaldehyde having a low water content represents the foundation for processes for preparing trioxane in the gas phase. A possible process which has been described is, for example, the nonoxidative dehydrogenation of methanol to formaldehyde using sodium-containing catalysts (DE 37 19055 A1, DD 264209 A1, JP 63079850, DE 3920811 A1, JP 02040237 A, JP 61130252 A, JP 59048429 A and DE 19644188 A1). The catalytically active species is presumed to be, inter alia, atomic sodium in the gas phase, which accelerates the dehydrogenation of methanol by a free radical mechanism (S. Ruf, G. Emig, Appl. Catal. A 1997, 161, 19–24).

As regards the conversion of formaldehyde having a low water content into trioxane, from AT 252913 and SV 20944 for example, disclose the preparation of trioxane from gaseous formaldehyde containing not more than 10% by weight of water using a Lewis acid ($FeCl_3$, $ZnCl_2$, $SnCl_4$, $BF_3$, $H_3PO_4$, $H_2SO_4$, ion exchangers, zeolites) applied to an inert support material ($SiO_2$, $Al_2O_3$ or wooden charcoal). The best catalyst was found to be silica gel impregnated with 10% by weight of sulfuric acid. The best values for the conversion of gaseous formaldehyde (62.5% in inert gas) were obtained at a temperature of 90° C. However, these conditions are, on the basis of today's state of the art, far away from industrial conditions: the reaction temperature is in the region of the polymerization limits of formaldehyde and the formaldehyde concentration is far from formaldehyde concentrations which can be achieved industrially by the nonoxidative dehydrogenation and/or further process steps. The nonoxidative dehydrogenation also achieves a water content in the formaldehyde of far below 10% by weight.

Significant industrial disadvantages of the catalyst system described result from its nature: catalysts which are prepared by impregnation of supports with liquid acids have a very low catalytically active surface area, since the pores of the support are filled with liquid. In addition, the acid is not chemically anchored to the support and is carried out from a fixed bed. This leads to progressive deactivation of the catalyst and to contamination of the product. There are also corrosion problems which make it necessary to use expensive, corrosion-resistant materials for plant construction.

EP 604884 A1 describes the trimerization of anhydrous formaldehyde over a vanadyl phosphate hemihydrate unsupported catalyst with a selectivity of almost 100% and a low activity (22.1% of the maximum achievable equilibrium conversion, space-time yield: 35.3 g/lh). At good selectivity, the activity of the catalyst is thus only moderate. As an unsupported catalyst, the catalyst is very expensive due to the high vanadium content and a complicated method of production (two wet chemical steps to get the active composition, drying, shaping, activation). In addition, the very low mechanical stability of the granulated vanadyl phosphate is a great disadvantage for industrial use.

EP 691338 A describes the use of the heteropolyacid $H_4PVMo_{11}O_{40}* n H_{20}$ (n=0–32) on an inert support material or pressed together with an inert filler for the trimerization of formaldehyde having a low water content. This catalyst displays a higher activity compared to the vanadyl phosphate hemihydrate (conversion close to the equilibrium conversion). Disadvantages such as rapid deactivation and high production costs stand in the way of the use of this catalyst.

EP 0691338 A1 describes a process for preparing trioxane in which a class of heteropolyacids having the composition $H_3PMo_mW_nO_{40}*xH_{20}$; n, m=4–8; n+m=12; x=0–32 in the form of a supported catalyst is used. Thus, a catalyst based on silicon carbide and the heteropolyacid $H_3PMo_6W_6O_{40}*xH_2O$ is said to convert anhydrous formaldehyde into trioxane at a selectivity of 99%, while 93% of the equilibrium conversion is achieved (space-time yield: 85.9 g/lh). Here too, rapid deactivation and the high price stand in the way of the use of this catalyst system.

Further disadvantages are that expensive support materials such as silicon carbide are required for the use of heteropolyacids as catalyst and the preparation of suitable heteropolyacids is costly, since they are not commercially available compounds and the synthesis of the heteropolyacids includes steps which cannot readily be scaled up (e.g. ether extraction).

Unpublished long-term tests carried out by the Applicant using supported heteropolyacids also indicated that use of these catalysts is not feasible under industrial conditions (high formaldehyde partial pressure): deactivation was observed and this led in the best case to an activity loss of 80% in a few days, but in some cases even to complete loss of the catalytic activity. The reason for this is very probably overreduction of the redox-active heteropolyacids. Regeneration experiments were only partly successful, since the mechanical stability of the supported catalysts also decreased significantly in the long-term test. As a result of this, abraded material was formed and led to blockage of the test reactors.

Phosphoric acid catalysts, in particular solid phosphorous acid catalysts (SPA catalysts) are used in petrochemical processes such as the preparation of cumene from benzene and propene or in the oligomerization of alkenes to form polygasoline. Their use for the trimerization of formaldehyde has not been described hitherto. For commercial applications, use is made predominantly of phosphoric acid catalysts based on silicon phosphate.

It is an object of the present invention to provide a catalyst system which has long-term stability, particularly under industrial conditions too, and can be used for the gas-phase trimerization of formaldehyde having a low water content. This catalyst system should also have a significantly improved operating life compared to the prior art, since a sufficient long-term stability is a decisive prerequisite for industrial implementation of the process. As regards the operating life problem, there has hitherto been no solution.

It has now surprisingly been found that SPA catalysts can advantageously be used for the gas-phase trimerization of formaldehyde to give trioxane, with the operating life problem being solved and the realization of an industrial process thus being made possible.

The invention accordingly provides a process for preparing trioxane, which comprises trimerizing gaseous formaldehyde having a low water content in a heterogeneously catalyzed gas-phase reaction using a solid phosphoric acid catalyst.

The gas-phase trimerization of formaldehyde according to the invention has a series of advantages over the (hitherto not yet practiced) prior art. At good selectivity and activity, the system displays excellent long-term stability. It has been pleasing to find that, according to the invention, it is possible to use even currently commercially available and inexpensive silicon phosphate catalysts which have already been optimized in terms of shaping (e.g. for cumene production) and whose mechanical stability both in the unused state and in test samples removed from the reactor is good.

The invention additionally provides for the use of solid phosphoric acid catalysts for the trimerization of formaldehyde in general and also provides an integrated process for preparing trioxane, comprising a nonoxidative dehydrogenation of methanol to form formaldehyde, an optional process step for purifying the formaldehyde, a gas-phase trimerization of the formaldehyde using a solid phosphoric acid catalyst and a separation step in which the trioxane is separated from unreacted formaldehyde and the unreacted formaldehyde is returned to the trimerization step.

For the purposes of the invention, formaldehyde having a low water content is formaldehyde containing from 0 to 5% by weight, preferably from 0 to 3% by weight, of residual water. The formaldehyde advantageously contains as little water as possible, i.e. it is almost or even completely anhydrous. The formaldehyde can comprise customary amounts of secondary constituents usual in its production. However, it is advantageous for the content of secondary components to be made as small as possible by means of appropriate preparation or work-up processes.

Solid phosphoric acid catalysts (SPA catalysts) and their production are generally known. Apart from silicon phosphate catalysts, boron phosphate, aluminum phosphate, zirconium phosphate, titanium phosphate and zinc phosphate catalysts having acidic properties have also been described (DE 2116922; EP 0469205 B1; J. Soria, J. E. Iglesias, J. Sanz, *J. Chem. Soc. Faraday Trans.* 1993, 89, 2515–2518; A. Tada, H. Itoh, Kitami Kogyo Daigaku Kenkyu Hokoku 1979, 11, 121–125). In addition, EP 0386845 B1 describes modification of a zirconium phosphate catalyst with organosulfonic acid groups, by means of which improved high-temperature stability is achieved.

In the process of the invention, SPA catalysts in general can be advantageously used. They can be used alone, in combination with other SPA catalysts or as shaped bodies, for example as granules, rings, pellets, spheres, rods, extrudates, etc., as powder or applied to an inert support. The catalyst may also be diluted with inert materials, for example to achieve a gradated bed in the reactor with its associated reaction engineering advantages. Dilution may be achieved either by mixing the shaped catalyst bodies with inert shaped bodies of similar size or by mixing and shaping pulverulent phosphoric acid catalysts with inert powders, with or without, use of binders.

The achievable activity, selectivity and stability generally depend on the choice of the catalyst material, the support material, the porosity (i.e. the pore volume) of the catalyst and also on the reaction conditions selected, which each have to be optimized. In principle, the SPA catalysts have similar activity and selectivity to heteropolyacids, but have a significantly improved long-term stability. The mechanical stability is significantly better than that of the supported heteropolyacid catalysts.

According to the present invention, preference is given to using silicon phosphate, boron phosphate, aluminum phosphate, zirconium phosphate, titanium phosphate, zinc phosphate or mixtures or mixed compounds thereof. Particular preference is given to using silicon phosphate.

The SPA catalysts are sensitive to the water content of the formaldehyde being too high. It is therefore advantageous to use formaldehyde having a residual water content of less than 10,000 vpm, preferably less than 5000 vpm. 1 vpm (volume part per million) corresponds to 1 part by volume per $10^6$ parts by volume, i.e. 1000 vpm=0.1% by volume. Advantageous SPA catalysts are those which are insensitive to a residual water content of 10,000 vpm, preferably 5000 vpm. It is also advantageous for the SPA catalyst to be able to be regenerated by thermal treatment and flushing so as to make up a drop in activity of selectivity.

The calculated content of phosphoric acid in the SPA catalyst is generally from 0.5 to 99% by weight, preferably from 1 to 90% by weight, based on the weight of the finished, dried catalyst composition.

The internal surface area of the SPA catalyst is generally from 0.001 to 50 $m^2/g$, preferably from 0.001 to 20 $m^2/g$. The SPA catalyst generally has a pore volume of from 0.01 to 1 $cm^3/g$, preferably from 0.05 to 0.8 $cm^3/g$. The proportion of the pore volume made up by micropores is advantageously less than 20%, in particular less than 10%.

The phosphoric acid catalyst can also be diluted with inert materials. This is particularly advantageous when a gradated bed in the reactor is desired for reaction engineering reasons. Dilution can be achieved by mixing shaped catalyst bodies with inert shaped bodies of similar size or by mixing and shaping pulverulent phosphoric acid catalysts with inert powders, either with or without use of binders.

The trioxane prepared by the process of the invention advantageously has a residual formic acid content of less than 0.5% by weight and a methyl formate content of less than 6% by weight. Such low residual contents are usually not achieved by other processes, so that appropriate additional purification or concentration is necessary before the polymerization to give POM.

The process of the invention is particularly suitable as a trimerization step in an integrated process comprising a nonoxidative methanol dehydrogenation to produce formaldehyde, a gas-phase trimerization according to the invention and a separation step for separating trioxane and unreacted formaldehyde. The formaldehyde can, if desired, be purified before the trimerization and the formaldehyde separated off in the separation step is returned to the trimerization step.

The process of the invention is advantageously carried out at reaction temperatures of from 80 to 160° C., preferably from 90 to 145° C., at an inlet partial pressure of the formaldehyde of from 0.5 to 5 bar absolute, preferably from 0.5 to 2 bar, and at an inlet concentration of formaldehyde of from 1 to 100% by volume, preferably from 20 to 100% by volume. The reaction can, if desired, be carried out in the presence of an inert carrier gas. Carrier gases which can be used are, for example, nitrogen, argon and carbon dioxide. Preference is given to using nitrogen.

The examples described below illustrate the invention without restricting its scope.

Reactor Test on the Gas-phase Trimerization of Anhydrous Formaldehyde to Give Trioxane The catalysts are tested in a fixed-bed tube reactor having a tube diameter of 2.9 cm and a length of 60 cm. The reactor is heated externally by means of oil jacket heating. 200 ml of the shaped catalyst bodies are placed in the reactor. The reactor volume upstream and downstream of the catalyst bed is filled with glass spheres. The test apparatus is controlled by a process control system and is operated continuously.

As source of anhydrous formaldehyde, use is made of trioxane (polymerization quality) in admixture with nitrogen (proportions: 71/29) which is catalytically decomposed to formaldehyde at a selectivity of >97% over vanadyl phosphate hemihydrate in an upstream reactor.

The reaction conditions in the tests are 108° C. wall temperature on the reactor, 1150 mbar absolute pressure. The feed gas stream is composed of 88% by volume of formaldehyde and 12% by volume of $N_2$. Full analysis of the output from the reactor is carried out on-line directly on the output from the reactor by means of a calibrated gas chromatograph (CG; 3 column arrangement).

In principle, the conversions and space-time yields reported in the following examples are capable of further optimization by appropriate choice of reaction parameters. Thus, the equilibrium of the reaction examined is sensitive to the formaldehyde partial pressure and the temperature.

The trimerization of formaldehyde is an exothermic reaction which proceeds with a large decrease in volume. The reaction equilibrium should accordingly be able to be shifted in the direction of trioxane by increasing the pressure and lowering the temperature. However, the opportunities of doing this are greatly limited by the pressure- and temperature-dependent polymerization limits of formaldehyde (formation of paraformaldehyde). In order to achieve a reliable and reproducible classification of the catalysts, the above-described reaction parameters were therefore selected.

The following parameters were determined from the GC data: conversion C, trioxane selectivity S, space-time yield STY.

EXAMPLE 1

A commercial silicon phosphate catalyst (C84-5, Süd-Chemie) was used without further pretreatment. The catalyst was in the form of extrudates (diameter: 5.5–7.5 mm, length: 8–14 mm) and, according to the manufacturer, contained 68–80% by weight of acid. The pore volume was 0.19 cm$^3$/g.

Reactor test: The catalyst was installed as described above. After heating to 108° C., the formaldehyde/nitrogen mixture was fed to the reactor. Steady-state operation was achieved after about 8 hours; the catalyst was examined over a total operating time of 85 hours.

| Experiment | Catalyst | Source | C % | S % | STY g/l*h | Deact. %/24 h | Hot spot ° C. | Hot spot position |
|---|---|---|---|---|---|---|---|---|
| WETR 26, 27 | H$_3$PO$_4$/ SiO$_2$ | Süd-Chemie | 41.4 | >96.2 | 82.4 | 0 | 125 | stable |

EXAMPLE 2

A commercial silicon phosphate catalyst (CA-131, Süd-Chemie) was used without further pretreatment. The catalyst was in the form of extrudates (diameter: 6–7 mm, length: 9–16 mm) and, according to the manufacturer, contained 81–83% by weight of acid. The pore volume was 0.23cm$^3$/g.

Reactor test: The catalyst was installed as described above. After heating to 108° C., the formaldehyde nitrogen mixture was fed to the reactor. Steady-state operation was achieved after about 8 hours; the catalyst was examined over a total operating time of 85 hours.

| Experiment | Catalyst | Source | C % | S % | STY g/l*h | Deact. %/24 h | Hot spot ° C. | Hot spot position |
|---|---|---|---|---|---|---|---|---|
| WETR 28 | H$_3$PO$_4$/ SiO$_2$ | Süd-Chemie | 39.8 | >95.4 | 78.5 | 0 | 125 | stable |

EXAMPLE 3

Production of the catalyst: 250 ml of SiO$_2$/Al$_2$O$_3$ pellets (about 5 mm, Norton SA 5223) were impregnated with 30 g of 85% strength phosphoric acid so that 90% of the pore volume of the support material was filled. The impregnated pellets were subsequently mixed for 15 minutes and then calcined at 250° C. for one hour.

Reactor test: The catalyst was installed as described above. After heating to 108° C., the formaldehyde nitrogen mixture was fed to the reactor. Steady-state operation was achieved after about 16 hours; the catalyst was examined over a total operating time of 36 hours.

| Experiment | Catalyst | Source | $C^1$ % | $S^1$ % | $STY^1$ g/l*h | Deact. %/24 h | Hot spot[1] °C. | Hot spot position |
|---|---|---|---|---|---|---|---|---|
| WETR 32 | $H_3PO_4$/ $SiO_2$/ $Al_2O_3$ | produced in-house | 28.4 | >98.4 | 58.0 | 19.5 | 125 | stable |

[1]After an operating time of 16 hours

EXAMPLE 4

Production of the catalyst: 250 ml of $TiO_2$ rings (about 5×5 mm, Norton XT90045) were impregnated with 40.8 g of 85% strength phosphoric acid so that 90% of the pore volume of the support material was filled. The impregnated rings were subsequently mixed for 15 minutes and then calcined at 250° C. for one hour.

Reactor test: The catalyst was installed as described above. After heating to 108° C., the formaldehyde/nitrogen mixture was fed to the reactor. Steady-state operation was achieved after about 6 hours; the catalyst was examined over a total operating time of 24 hours.

| Experiment | Catalyst | Source | C % | S % | STY g/l*h | Deact. %/24 h | Hot spot °C. | Hot spot position |
|---|---|---|---|---|---|---|---|---|
| WETR 30 | $H_3PO_4$/ $TiO_2$ | produced in-house | 39.7 | >97.4 | 80.0 | 0 | 124 | stable |

COMPARATIVE EXAMPLE 1

Production of the catalyst: 250 ml of aluminum oxide spheres (about 5 mm, Norton SA 5262) were impregnated with an aqueous solution of 5 g of $H_3PMo_5W_7O_{40}$ using the pore filling method and were mixed for 10 minutes. The major part of the water was subsequently taken off from the impregnated shaped bodies by means of a rotary evaporator. The catalyst was finally dried at 150° C. for 12 hours.

Reactor test: The catalyst was installed as described above. After heating to 108° C., the formaldehyde/nitrogen mixture was fed to the reactor. Steady-state operation was not achieved even after about 100 hours; the catalyst was examined over a total operating time of 100 hours.

| Experiment | Catalyst | Source | $C^1$ % | $S^1$ % | $STY^1$ g/l*h | Deact. %/24 h | Hot spot[1] °C. | Hot spot position |
|---|---|---|---|---|---|---|---|---|
| WETR 21 | HPA/α- $Al_2O_3$ | produced in-house | 45.0 | >96.7 | 90.0 | 16 | 115 | wanders |

[1]After an operating time of 8 hours

COMPARATIVE EXAMPLE

Production of the catalyst: 250 ml of silicon carbide rings (5×5 mm, Norton SC 5532) were impregnated with an aqueous solution of 5 g of $H_3PMo_5W_7O_{40}$ using the pore filling method and were mixed for 10 minutes. The major part of the water was subsequently taken off from the impregnated shaped bodies by means of a rotary evaporator. The catalyst was finally dried at 150° C. for 12 hours.

Reactor test: The catalyst was installed as described above. After heating to 1 08° C, the formaldehyde/nitrogen mixture was fed to the reactor. Steady-state operation was not reached; the catalyst was examined over a total operating time of 24 hours.

| Experiment | Catalyst | Source | C¹ % | S¹ % | STY¹ g/l*h | Deact. %/24 h | Hot spot¹ °C | Hot spot position |
|---|---|---|---|---|---|---|---|---|
| WETR 33 | HPA/ SiC | produced in-house | 29.9 | 91.2 | 56.7 | 25 | 114 | wanders |

[1]After an operating time of 8 hours

What is claimed is:

1. A process for preparing trioxane, which comprises trimerizing gaseous formaldehyde having a low water content in a heterogeneously catalyzed gas-phase reaction using a solid phosphoric acid catalyst.

2. The process as claimed in claim 1, wherein the solid phosphoric acid catalyst is silicon phosphate, boron phosphate, aluminum phosphate, zirconium phosphate, titanium phosphate, zinc phosphate or a mixture thereof.

3. The process as claimed in claim 1, wherein the residual water content of the formaldehyde having a low water content is less than 10,000 vpm, or less than 5000 vpm.

4. The process as claimed in claim 1, wherein the phosphoric acid catalyst is insensitive to residual water contents in the formaldehyde of less than or equal to 10,000 vpm, or less than or equal to 5000 vpm.

5. The process as claimed in claim 1, wherein the phosphoric acid catalyst is regenerated by thermal treatment and flushing with nitrogen when the activity or selectivity drops.

6. The process as claimed in claim 1 carried out at a reaction temperature in the range from 80 to 160° C., an inlet partial pressure of formaldehyde of from 0.5 to 5 bar and an inlet concentration of formaldehyde of from 1 to 100%.

7. The process as claimed in claim 1, wherein the reaction is carried out in the presence of an inert carrier gas, or nitrogen, argon or carbon dioxide.

8. The process as claimed in claim 1, wherein the content of phosphoric acid in the phosphoric acid catalyst is from 0.5 to 99% by weight, based on the finished catalyst composition.

9. The process as claimed in claim 1, wherein the phosphoric acid catalyst has an internal surface area of from 0.001 to 50 $m^2$ and a pore volume of from 0.01 to 1 $cm^3$.

10. The process as claimed in claim 1, wherein the proportion of the pore volume made up by micropores in the solid phosphoric acid catalyst is less than 20%, or less than 10%.

11. The process as claimed in claim 1, wherein the phosphoric acid catalyst is as a shaped body.

12. The process as claimed in claim 1, wherein the phosphoric acid catalyst is diluted with inert materials.

* * * * *

UNITED STATES PATENT AND TRADEMARK OFFICE
CERTIFICATE OF CORRECTION

PATENT NO. : 6,313,323 B1  
DATED : November 6, 2001  
INVENTOR(S) : Harald Werner, Elke Schweers, Frank Olschewski, Gerard Geiss, Elfriede Hufsky, Helmut Tränkler and Heinz Alexander Page 1 of 1

It is certified that error appears in the above-identified patent and that said Letters Patent is hereby corrected as shown below:

Column 1,  
Line 48, delete "20944" and insert -- 209441 --.

Column 2,  
Line 21, delete "$H_{20}$" and insert -- $H_2O$ --.  
Line 31, delete "$H_{20}$" and insert -- $H_2O$ --.

Signed and Sealed this

Ninth Day of April, 2002

Attest:

*Attesting Officer*

JAMES E. ROGAN  
*Director of the United States Patent and Trademark Office*